(12) United States Patent
Welchman et al.

(10) Patent No.: US 6,809,822 B2
(45) Date of Patent: *Oct. 26, 2004

(54) APPARATUS AND METHOD FOR AUTOMATED GAME BALL INSPECTION

(75) Inventors: Kenneth A. Welchman, Tiverton, RI (US); Steven A. Bresnahan, Dartmouth, MA (US); Henry James Conaty, Jr., Dighton, MA (US)

(73) Assignee: Acushnet Company, Fairhaven, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/292,634

(22) Filed: Nov. 13, 2002

(65) Prior Publication Data

US 2003/0090659 A1 May 15, 2003

Related U.S. Application Data

(63) Continuation of application No. 09/372,881, filed on Aug. 12, 1999, now Pat. No. 6,630,998, which is a continuation-in-part of application No. 09/133,712, filed on Aug. 13, 1998, now abandoned.

(51) Int. Cl.[7] .............................................. G01B 11/00
(52) U.S. Cl. ........................ 356/394; 382/141; 382/149
(58) Field of Search ................................ 356/392, 394, 356/426, 601, 606, 607–608, 429–431, 237.1–237.4; 250/223 R, 330; 382/149, 107, 110, 289, 141

(56) References Cited

U.S. PATENT DOCUMENTS

| | | | |
|---|---|---|---|
| 2,278,800 A | 4/1942 | Rodanet | 209/82 |
| 2,701,055 A | 2/1955 | Strom, Jr. | 209/111 |
| 2,778,497 A | 1/1957 | Bickley | 209/72 |
| 3,565,248 A | 2/1971 | Messerschmidt | 209/73 |
| 3,675,015 A | 7/1972 | Geib | 250/71 R |
| 3,930,063 A | 12/1975 | Miller et al. | 427/54 |
| 3,940,952 A | 3/1976 | Mitchell | 73/67.8 R |
| 4,110,047 A | 8/1978 | Takahashi | 356/200 |
| 4,259,013 A | 3/1981 | Faxvog et al. | 356/237 |
| 4,289,032 A | 9/1981 | Tominaga et al. | 73/599 |
| 4,358,202 A | 11/1982 | Puffer et al. | 356/430 |
| 4,398,825 A | 8/1983 | Lewis | 356/426 |
| 4,469,442 A | 9/1984 | Reich | 356/364 |
| 4,469,713 A | 9/1984 | Schwiecker et al. | 427/10 |

(List continued on next page.)

FOREIGN PATENT DOCUMENTS

| | | | |
|---|---|---|---|
| GB | 2228 315 | * | 8/1990 |
| GB | 2 228 315 | | 8/1990 |
| JP | 06 016 844 | | 1/1994 |
| JP | 06016844 | * | 1/1994 |
| JP | 8-309262 | | 11/1996 |
| JP | 8-318186 | | 12/1996 |
| JP | 9-61363 | | 3/1997 |
| JP | 9-61364 | | 3/1997 |
| JP | 9-292349 | | 11/1997 |
| JP | 9-326034 | | 12/1997 |

*Primary Examiner*—Frank G. Font
*Assistant Examiner*—Sang H. Nguyen
(74) *Attorney, Agent, or Firm*—Swidler Berlin Shereff Friedman, LLP

(57) ABSTRACT

An automated game ball inspection apparatus and system for determining quality of surface treatments applied to the surface of game balls. The inspection system includes an imaging system including a detector for creating and providing an image signal of the ball being inspected to an analyzer. The inspection system also includes an environmental modification device to account for contours on the spherical surface of the ball such that the imaging system can create and analyze still images of the ball. A sorter or reject device, may be provided to act upon the ball based on an output signal from the analyzer.

15 Claims, 8 Drawing Sheets

U.S. PATENT DOCUMENTS

| | | | |
|---|---|---|---|
| 4,641,966 A | 2/1987 | Lemmers et al. | 356/237 |
| 4,726,898 A | 2/1988 | Mills et al. | 209/545 |
| 4,814,198 A | 3/1989 | Baecklund | 427/9 |
| 4,969,361 A | 11/1990 | Kawasaki et al. | 73/593 |
| 5,118,194 A | 6/1992 | Mather et al. | 356/426 |
| 5,166,985 A | 11/1992 | Takagi et al. | 382/8 |
| 5,278,635 A | 1/1994 | Ono et al. | 356/430 |
| 5,286,532 A | 2/1994 | Yoshikawa et al. | 427/356 |
| 5,395,174 A | 3/1995 | Koch et al. | 400/611 |
| 5,443,642 A | 8/1995 | Bienduga | 118/688 |
| 5,457,326 A | 10/1995 | Tsujita et al. | 250/559.42 |
| 5,580,318 A | 12/1996 | Weber | 473/137 |
| 5,602,646 A | 2/1997 | Bernardin et al. | 356/426 |
| 5,611,723 A * | 3/1997 | Mitoma et al. | 451/6 |
| 5,632,205 A * | 5/1997 | Gordon et al. | 101/483 |
| 5,658,619 A | 8/1997 | Kirschner et al. | 427/512 |
| 5,667,840 A | 9/1997 | Tingey et al. | 427/8 |
| 5,703,687 A | 12/1997 | Kumagai et al. | 356/426 |
| 5,732,147 A * | 3/1998 | Tao | 382/110 |
| 5,755,335 A | 5/1998 | Michelotti et al. | 209/528 |
| 5,777,244 A | 7/1998 | Kumagai et al. | 73/865.8 |
| 5,848,189 A | 12/1998 | Pearson et al. | 382/218 |
| 5,859,923 A | 1/1999 | Petry, III et al. | 382/141 |
| 5,960,098 A | 9/1999 | Tao | 382/110 |
| 5,966,213 A * | 10/1999 | Shimosaka et al. | 356/613 |
| 5,985,370 A * | 11/1999 | Ohira et al. | 427/387 |
| 6,031,933 A * | 2/2000 | Kumagai | 382/141 |
| 6,061,086 A | 5/2000 | Reimer et al. | 348/125 |
| 6,201,892 B1 | 3/2001 | Ludlow et al. | 382/149 |
| 6,248,804 B1 * | 6/2001 | Lutz | 523/160 |
| 6,271,520 B1 * | 8/2001 | Tao et al. | 250/330 |
| 6,319,563 B1 | 11/2001 | Skrabski et al. | 427/511 |
| 6,462,812 B1 | 10/2002 | Heene et al. | 356/237.1 |
| 6,630,998 B1 * | 10/2003 | Welchman et al. | 356/394 |

* cited by examiner

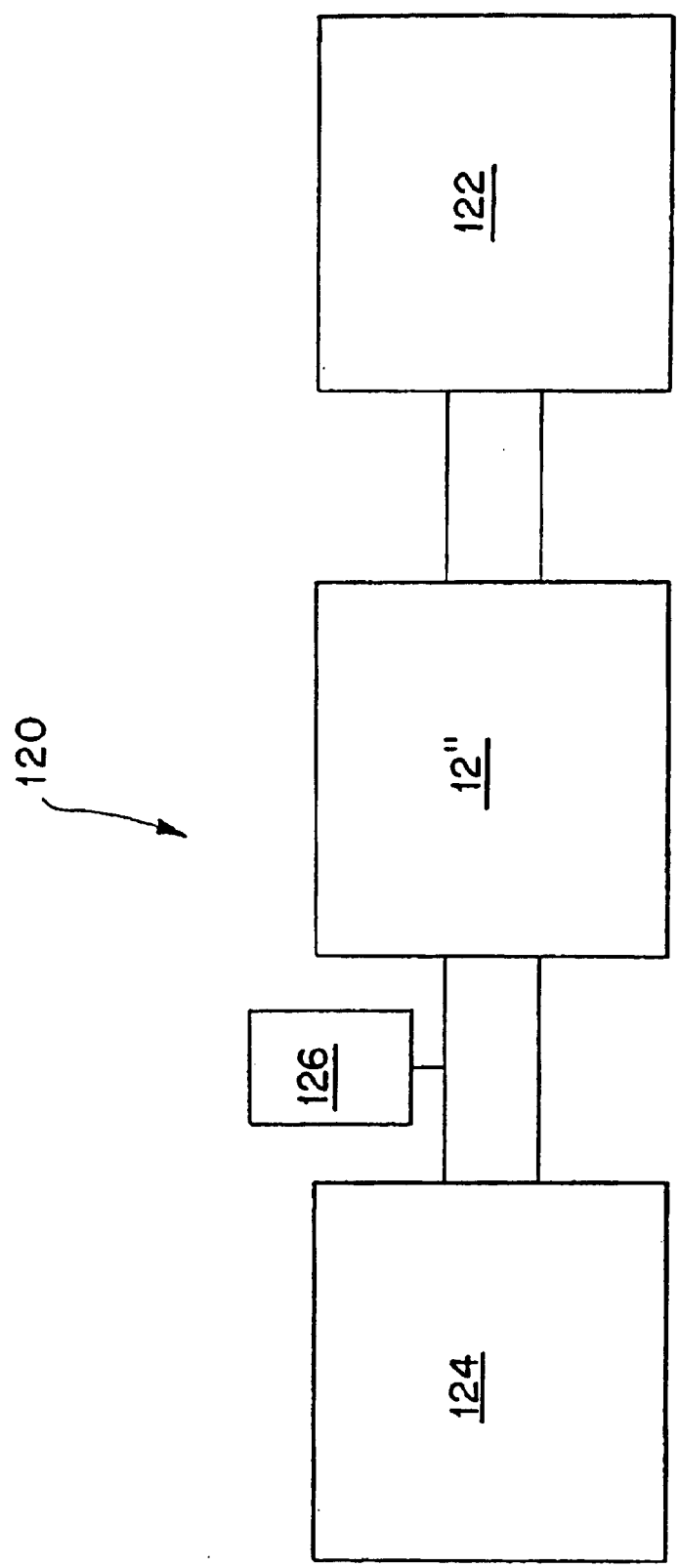

APPARATUS AND METHOD FOR AUTOMATED GAME BALL INSPECTION

This application is a continuation of U.S. patent application Ser. No. 09/372,881, filed Aug. 12, 1999, now U.S. Pat. No. 6,630,998, which is a continuation-in-part of U.S. patent application Ser. No. 09/133,712, filed Aug. 13, 1998, ABN, the entire disclosures of which are incorporated herein by reference.

FIELD OF THE INVENTION

The present invention generally relates to a system for and method of automating the inspection of game balls. More particularly, the present invention relates to an automated system for and method of inspecting treatments applied to the surface of a golf ball.

BACKGROUND OF THE INVENTION

The manufacture of golf balls typically involves a series of sequential processes performed at different processing stations, typically spatially separated one from another. For example, golf balls typically have a core and a dimpled cover formed thereover.

The golf ball cover typically contains a white or other colored concentrate, or is painted. Further, indicia (such as a ball number, a ball brand name, and/or a company name) can be applied to the surface, such as by pad-printing, thereon. A clear protective coat is commonly applied over the production print to enhance the appearance of the finished golf ball (such as by providing a shiny exterior) and to improve durability. A prime coat, typically a film about one-half the thickness of the clear coat, may be applied before production printing or over the production print and before the application of the clear coat. The prime coat prevents running or smearing of typical ink indicia.

Typically, golf balls which have just been covered with a clear coat are transported from a clear coat spray paint booth to a separate drying station at a remote location. Additional printing, such as a logo, may be applied over the cured clear coat.

Each process must be carefully monitored for quality assurance purposes. Inspections are typically performed for assuring a desired confidence level in production quality. Quality control criteria, may be in place as well. The manufacturer may further choose to manually inspect the entire lot being inspected if a given number of defective balls are found therein. Moreover, if a major defect, such as a gross cosmetic defect or a defect affecting performance or durability, is found the manufacturer may choose to shut down the entire system.

There has been a continuing desire to achieve high production rates. Because automated apparatuses typically may function faster than human operators, there has been an ongoing goal to reduce, if not eliminate, human intervention during the manufacturing process. Thus, each of the above processes is typically performed at a separate automated processing station functioning at optimal efficiency and speed so that the overall production rate is maintained at the desired high level. For instance, pad-printing apparatus preferably includes an array of print-pads arranged to apply a production print sequentially on various locations on the surface of the golf ball, the golf ball being indexed before being passed to the next print-pad.

The clear coating process preferably is performed by an automated spray painting technique utilizing a spray paint booth with one or more spray paint guns. A quick drying clear coat paint having a catalyzing agent (such as a solvent that dissipates quickly to dry the clear coat) may be used to reduce the usual clear coat drying time of about ten hours to about one and one-half hours.

Automation of the manufacturing process gives rise to various types of manufacturing defects. For example, automated pad-printing equipment may create smudges from excess ink carried by the printing pad. Other production print defects occur, as well. Vibration or improper set-up, such as improper positioning or accidental switching of the paint supply hoses (resulting in cut-off of paint supply to the respective spray guns), of the spray gun of an automated paint spray booth results in defectively coated golf balls. Moreover, the clear coat paint may periodically clog the spray booth filter, interfering with proper spraying of paint therefrom to coat the golf ball. As long as the improper functioning of the processing station continues, an increasingly larger number of improperly treated golf balls are produced.

One particular instance in which inspection of the results of a process shortly after completion is important is in the clear coat spray painting operation. Clear coated golf balls have been transported on a tray, via a material handling truck, from the clear coat station to a drying room to be cured for approximately ten hours. A recent improvement in the clear coat application process is the use of a fast-drying clear coat which hardens quickly (approximately one and one-half hours). However, catalyzation may occur even in the spray paint booth, resulting in a thick brittle coating on the spray booth filter and increasing the probability of spray paint operation malfunctions. Such malfunctions as clogging of spray guns and gelling of the clear coat during use result in inadequate clear coating of the golf ball. Moreover, transfer of the freshly coated golf ball into the curing station before inspection does not alert the operator to attend to unacceptable spray painting apparatus conditions until nearly two hours later. Thus, ever increasing production rates further increase the need to identify defective products early on in the treatment process.

Given the quality control standards necessary to meet production standards and the high production rates of golf ball manufacturing plants, actions to correct a malfunction in the automated processing equipment should be taken as soon as possible to reduce the number of defective golf balls produced. The sooner a defect is detected, the lower the likelihood of reaching the predetermined number of defects initiating a need for further quality assurance corrective measures, as described above, to be taken. Accordingly, there is a need for speedy and efficient inspection of golf balls so that any manufacturing problem may be corrected almost immediately to reduce the further production of defective balls.

A variety of automated inspection systems and methods are known for use in quality control of automated processing stations, such as for coating, finishing, or otherwise affecting the surface appearance of products. For example, U.S. Pat. No. 5,665,840 to Tingey et al. discloses a method of detecting the coverage of a lubricant coating on a non-spherical article. Inspection apparatuses currently known for inspecting spherical objects generally require rotation of the object and cannot account for the three-dimensional contoured surface. For example, U.S. Pat. No. 5,703,687 to Kumagai et al. shows an automated inspection system which requires the addition of golf ball rotating equipment to the usual automated conveying equipment used to convey golf balls from an automated processing apparatus.

The spherical shape of the golf ball makes automated inspection of the three-dimensional surface difficult to achieve by the two-dimensional analysis techniques of inspection systems used in other industries. The addition of contours, in the form of dimples, on an already spherical object further complicates automated inspection thereof. Standard machine vision inspection systems using a template based inspection technique desensitized to prevent false rejections of prints or contoured surfaces are also desensitized to small defects on the edge of the print and thus are not completely effective. Prior art inspection systems have not been successful at achieving the proper combination of machine vision components, lighting, optics, and image processing techniques necessary to successfully analyze the printed images on golf balls to provide an on-line inspection system.

Thus, the golf ball manufacturing industry has heretofore relied on manual inspection to determine the quality of the various processes performed in manufacturing a golf ball. However, because the high production rate typically encountered in the industry far exceeds the speed with which manual inspection can be performed, such manual inspection cannot be performed on every ball, thus impeding efficiency, and potentially resulting in a certain number of undetected defective balls. Moreover, manual inspection is not 100% effective, given the possibility of human error or oversight, and may cause the inspected ball to be marred by the manual handling.

Thus, although automation of the golf ball manufacturing process has resulted in high production rates, such production rates are subject to the efficiency and speed with which quality inspection may be performed. If inspection is not performed routinely and quickly, a high number of defective products may be produced before appropriate measures are taken to correct the cause of the defect.

SUMMARY OF THE INVENTION

In accordance with the principles of the present invention an automated inspection system is provided in one or more game ball processing stations in an assembly line. The automated inspection system may be used to monitor the manufacture of golf balls, such as for quality control purposes. Thus, the automated inspection system of the present invention may be used to determine conformity to predetermined standards. Moreover, the application of an automated inspection system permits monitoring of 100% of the game balls, in-line with the processing apparatus of a given processing station, so that early signs of undesirable station conditions can be attended.

The automated inspection system of the present invention is comprised of an imaging system which is adapted to account for unique surface properties, such as contours, of a golf ball to analyze various characteristics of a surface treatment (e.g., contouring or coloring) of the golf ball. In a preferred embodiment, the automated inspection system of the present invention is used to detect and analyze a surface treatment, such as the application of a coating or paint to the surface of a golf ball, affecting the cosmetic or aesthetic appearance of the golf ball. For example, the distribution (e.g., uniformity and symmetry), adequacy (e.g., degree, thickness, or quantity), and accuracy (e.g., the specific form of a printed symbol) with which a surface treatment has been applied to the surface of a golf ball may be viewed by an imaging system. The imaging system transmits a clear, undistorted image of the ball being inspected to an analyzer which analyzes various characteristics of the substance which has been applied to the golf ball.

The system preferably includes an environmental modification device to modify inspection conditions so that an accurate image is presented and/or transmitted to the imaging system. For example, the environmental modification device can be a modification to the lighting to eliminate glare and thus eliminate false readings, or to account for surface distortions caused by the unique spherical, dimpled exterior surface of a golf ball such that a two-dimensional analysis of the three-dimensional surface is possible. For example, in a preferred embodiment, a clear coat coverage is inspected by monitoring the presence of an agent provided in the clear coat and detectable under non-ambient conditions, such as ultraviolet ("UV") lighting. Thus, the environmental modification device is ultraviolet lighting and, preferably, a plurality of ultraviolet lights positioned above and below the imaging system to provide proper illumination of the ball for the imaging system.

The system of the invention may be used to inspect a variety of additional processing steps during golf ball manufacture with appropriate modifications being made to correspond to the particular nature of the process being inspected.

The imaging system provides a detection signal to an analyzer. The analyzer compares the detection signal with a predetermined standard to determine if the game ball meets predetermined quality standards.

Preferably, the analyzer of the present invention generates a control signal depending on the results of the analysis of the surface treatment being detected. The control signal is used to remove defective products from the process. If a defective product is detected, the inspection system of the present invention also preferably emits a warning signal so that operators can attend to the cause of the defect immediately after the defective product has been processed and inspected. If desired, a computer may keep track of all products being processed so that as the product arrives at a processing station, the computer identifies the product such as to determine whether further processing should be performed.

The application of an automated inspection system in at least one processing station in a golf ball manufacturing plant permits golf balls processed in that station to be transferred automatically, thus minimizing ball-to-ball and ball-to-surface contact which otherwise occurs during transfer. Preferably, a plurality of processing stations are linked together such that golf balls are transferred automatically from station to station. The application of the automated inspection system to such linked processing stations permits automated inspection without requiring human interference.

Also in accordance with the principles of the present invention, a curing apparatus required to cure the surface treatment applied to the golf ball may be formed as a part of the automated processing station. Thus, a single processing station, having a surface treatment application apparatus and a curing apparatus, such as an oven, can be provided. In such a combined processing station, an inspection system formed in accordance with the principles of the present invention preferably is provided between the application apparatus and the curing apparatus such that inspection occurs as the balls are automatically passed from one to the other. Thus, defects are detected long before the curing process has been completed.

BRIEF DESCRIPTION OF THE DRAWINGS

The detailed description will be better understood in conjunction with the accompanying drawings, wherein like reference characters represent like elements, as follows:

FIG. 7 is a schematic diagram of a clear coat system station formed in accordance with the principles of the present invention.

DETAILED DESCRIPTION OF THE INVENTION

Figure 1A:
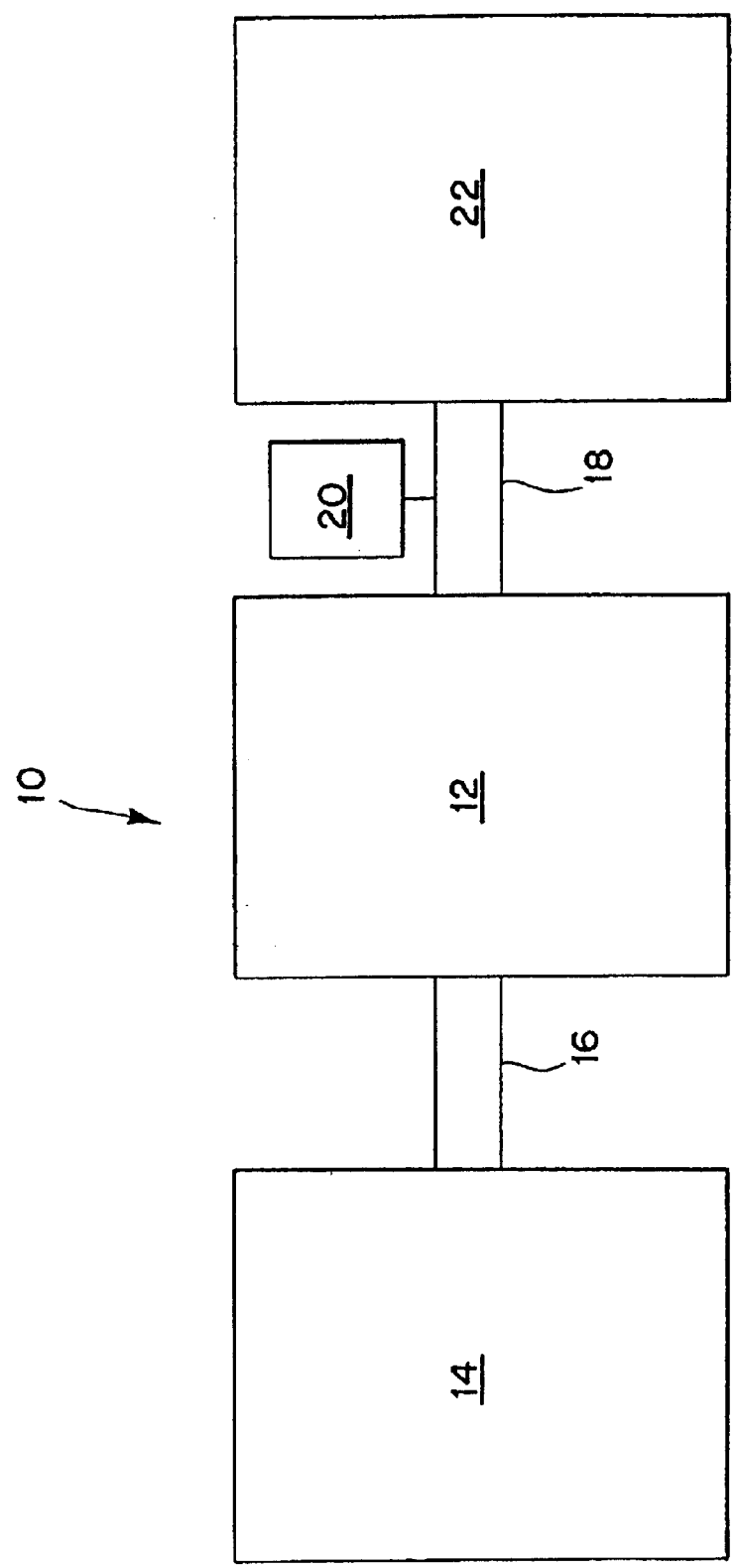
FIG. 1A is a schematic diagram of an automated processing station including an automated inspection system arranged and formed in accordance with the principles of the present invention and an inspection responsive device positioned to operate soon after the ball is inspected.

As shown schematically in FIG. 1, the present invention relates to the modification of one or more automated game ball processing stations 10 of a ball manufacturing process to include an automated inspection system 12. Automated inspection system 12 permits continuous, objective inspection of all of the balls being processed by automated processing apparatus in station 10 without interrupting or slowing down or otherwise interfering with processing and production of the balls. Automated inspection system 12 not only provides important information for use in quality control, but also permits further automated actions to be taken with respect to the balls being processed, as described herein. Thus, in accordance with the principles of the present invention, the ball manufacturing process is further streamlined and production speed and efficiency are increased.

In a preferred manufacturing process according to the present invention, processing station 10 has a processing apparatus 14 which carries out a particular golf ball surface treating operation during the manufacture of golf balls. For example, processing apparatus may treat the golf ball surface by applying a substance such as primer, coating, ink or paint to the surface of the golf ball as described in further detail below. After being processed by processing apparatus 14, the golf balls are transferred, preferably by a first automated transferring mechanism 16, directly from processing apparatus 14 to automated inspection system 12 positioned downstream and along the production line of processing apparatus 14. First automated transferring mechanism 16 may be a conveyor belt or a robotic arm or other form of a preferably automated mechanism that can transfer a product from a first processing station to another station, such as inspection system station as in the present invention, as well known to those of ordinary skill in the art, so that human handling and intervention are unnecessary. Preferably, a second automated transferring mechanism 18 is provided to automatically remove golf balls inspected by inspection system 12. It will be appreciated that automated transferring mechanisms 16 and 18 may be two portions of a single automated transferring mechanism. Thus, golf balls are quickly moved into position for inspection by inspection system 12 and also are quickly removed from inspection system 12 upon completion of inspection so that the next golf ball processed by processing apparatus 14 may be inspected immediately thereafter and any malfunctions of processing apparatus 14 will become known substantially immediately.

Preferably, an inspection responsive device 20 is provided to act on the inspected golf ball depending on the determinations made as a result of the inspection. Accordingly, in one embodiment, depicted in FIG. 1A, inspection responsive device 20 preferably is positioned to act on a ball soon after it exits inspection system 12. In yet another embodiment, depicted in FIG. 1B, inspection responsive device 20 may be positioned to act on a ball after additional processing steps have been performed on the ball by another processing apparatus 22. Such additional processing steps, which may include, without limitation, drying a printed surface or curing a substance applied to the ball, may occur at processing station 10 or at any other time after inspection.

Inspection responsive device 20 may perform any desired action on a golf ball which has been inspected by inspection system 12. For example, inspection responsive device 20 may be a reject device which rejects any golf ball inspection system 12 has determined does not meet production standards. Alternatively, inspection responsive device 20 may be a transfer device which transfers the inspected golf ball depending on conformance or nonconformance with production standards, such as a lever activated by a control signal to divert defective balls from further processing. Thus, a ball that does not meet production standards is removed, in any desired manner and at any desired time after inspection.

Figure 1B:
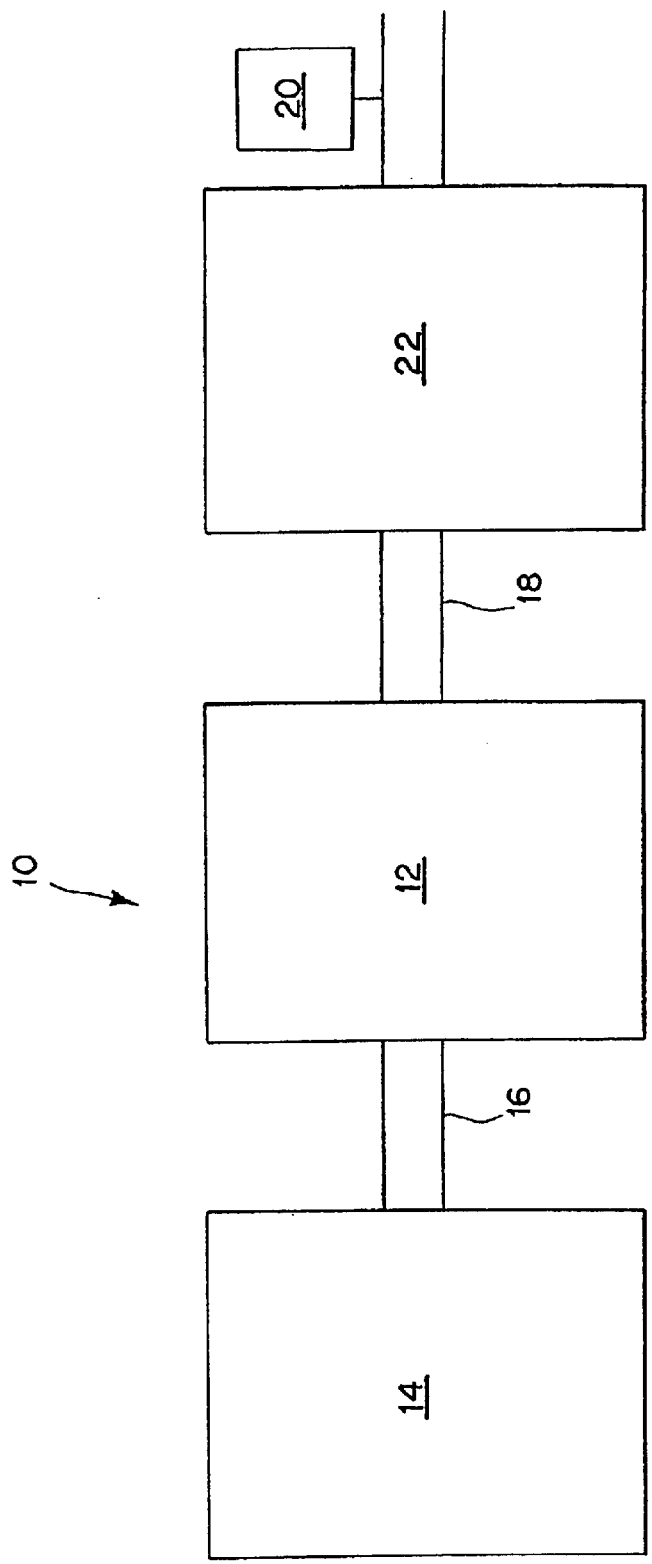
FIG. 1B is a schematic diagram of an automated processing station including an automated inspection system arranged and formed in accordance with the principles of the present invention and an inspection responsive device positioned to operate after additional processing steps have been performed on the ball.

In one embodiment rejected balls are removed from processing station 10 while golf balls meeting production standards continue on to additional automated transferring mechanism 18 for transfer either to another processing apparatus 22 or out of station 10. A transfer device, referenced herein as a "pick-and-place" device, may be used to individually transfer either the rejected or accepted ball, as described in further detail below. Alternatively, a computer may keep track of each ball and actuate a diverter or other such mechanism at a later point in the production line to separate rejected and accepted balls, as shown in FIG. 1B and described in further detail below.

Each golf ball that has undergone inspection by inspection system 12 may be transferred or conveyed by second automated transferring mechanism 18 to apparatus 22 for further processing. Apparatus 22 may be a further processing apparatus preferably provided within station 10 so that the golf balls need not be transferred for further processing, as described in greater detail below. Apparatus 22 also may be in the form of a transfer system provided to remove the golf balls from processing station 10 for further processing.

As will be appreciated, in accordance with the principles of the present invention, the above-described inspection system 12 as described above may be used in any of the various processing stations 10 through which a game ball is passed during manufacture. Because each processing station 10 performs a different process, inspection system 12 typically is modified to account for the specific nature of the process being performed. For instance, processes which involve printing on or coating or painting of the golf ball will require analysis of the surface characteristics, but not necessarily the shape or contour, of the ball. In contrast, processes which involve the shaping or forming of a layer of the golf ball will require analysis of the shape or contour of the ball.

Figure 2:
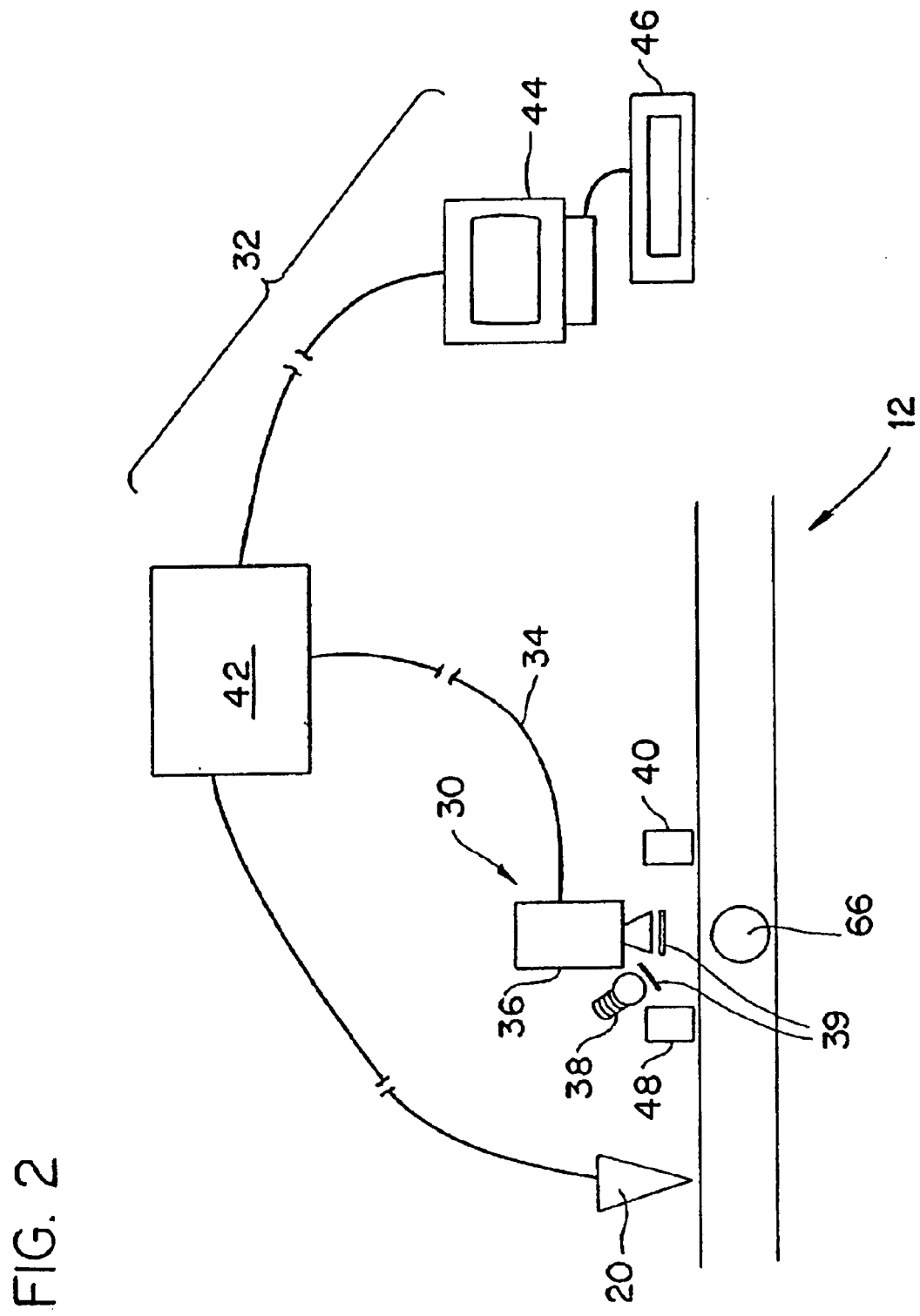
FIG. 2 is a schematic illustration of an automated inspection system formed in accordance with the principles of the present invention.

Referring to FIG. 2, in a preferred embodiment, automated inspection system 12 comprises an imaging system 30 and an automated analyzer 32 linked together preferably via an electronic link 34. In the preferred embodiment, imaging system 30 views and detects a golf ball to be inspected and provides a detection signal, such as an image of the golf ball, into automated analyzer 32. Analyzer 32 receives the detection signal and uses the signal to perform various analysis tasks such as analysis of the signal, statistics processing, task scheduling, generation of reject signals or further control signals, and/or alarms. Analyzer 32 may be placed near, and most preferably adjacent, processing station 10 so that the operator has easy and quick access to both the analyzer 32, to determine the defect, and the production line, to attend to and to correct the cause of the defect.

Imaging system 30 preferably includes detecting apparatus 36 (e.g., a camera or a photocell) for viewing the ball to be inspected. An environment modification device 38, further described below, may be provided to account for viewing or environmental conditions which may adversely affect automated inspection of golf balls 66. A product sensor 40 may also be included in imaging system 30 to trigger the inspection and analysis process. The product sensor 40 is used to prevent extraneous information (such as a scan of an empty space, i.e., without a golf ball) from being transmitted and analyzed by analyzer 32 so that statistics on acceptable and defective golf balls being scanned will not be skewed. Product sensor 40 may be any desired sensor, such as an optical or magnetic sensor that detects the presence of an object within range of the detecting apparatus 36, a fiber optic through beam product sensor which transmits a signal upon the passing of an object across its beam, a photoelectric eye, or a proximity switch. Product sensor 40 preferably is provided for each detecting apparatus 36.

Detecting apparatus 36 detects a visual image of an object and transmits such image for processing by analyzer 32. Optionally, detecting apparatus 36 (or analyzer 32) also records the image of the inspected golf ball for future reference. Detecting apparatus 36 may include a camera, a photocell, or other such automated detecting apparatus which generates or creates an image of an object presented thereto. Preferably, detecting apparatus 36 permits generation of electrical signals that are readily transferred and processed by automated analyzer 32. For instance, detecting apparatus 36 may include one or two high resolution, preferably electronically shuttered, solid state CCD (charged coupled device) monochrome or color cameras, depending on the process being inspected, as described in further detail below. Each camera preferably supplies high resolution images to analyzer 32. The physical resolving power is dependent on the camera's field of view and distance from the ball surface. For instance, a one inch field of view can be depicted by hundreds of thousands of pixels, each having a wide range of colors or shades of gray. Thus, differences in golf ball color or shading, such as caused by the application of a surface treatment such as a coating, ink or paint to the golf ball surface, may be detected electronically.

Because the different features of a golf ball to be analyzed may not be readily viewed by a commercially available detecting apparatus 36 because of certain viewing or environmental conditions, particularly if under ambient conditions, environment modification device 38 is provided to modify inspection conditions and thereby facilitate viewing by detecting apparatus 36 of the golf ball being inspected. As described in greater detail below, environment modification device 38 may, for example, include a custom lighting system which alters the lighting conditions so that visual features of the exterior surface of the golf ball or a substance applied to the exterior surface of the golf ball can be properly detected by detecting apparatus 36. In one embodiment, environment modification device 38 utilizes a plurality of LEDs in different colors to achieve greater and more intense illumination of golf ball 66, such as for facilitating inspection of printed matter on the surface of golf ball 66. Preferably, the LED colors are red, green, and blue so that in combination a white light is produced. Polarizing filters may be positioned between environment modification device 38 and golf ball 66 and/or between golf ball 66 and detecting apparatus to reduce glare that may occur when golf ball 66 is illuminated. Alternatively, or in addition to the use of polarizers, blowers may be used to dry the inspected surface prior to inspection in order to further reduce glare. In another embodiment, environment modification device 38 illuminates golf ball 66 with UV light, such as to detect the presence of a substance, such as a coating, applied to the surface of golf ball 66.

As discussed above, detecting apparatus 36 of imaging system 30 transmits the image it has generated to analyzer 32. Analyzer 32 includes at least a high speed vision engine 42, preferably including a computer processor, and a monitor 44, or other display means. A keyboard 46 or other means for interacting with vision engine 42 (an interface mechanism) preferably is also included. Vision engine 42 analyzes the image transmitted thereto by detecting apparatus 36 to determine the quality of the process performed by processing apparatus 14. Analysis typically involves a comparison of the detected image with a reference image. The precision and sensitivity of the analysis may be determined by the user.

A variety of inspection routines may be performed by vision engine 42, such as finding the center of the product, checking overall dimensions and contours, inspecting for contamination, and/or determining various characteristics of a surface treatment such as an application of a substance (e.g., primer, coating, ink or paint) to the surface of the golf ball. Because a variety of different aspects of the golf ball are inspected and analyzed, different areas on the surface of the golf ball must be inspected, and a variety of different, potentially overlapping, inspection routines are performed to provide the data necessary for the inspection analysis. The specific inspection routine performed on the golf ball is selected based on the process being inspected, as will be described in further detail below in connection with exemplary applications of the principles of the present invention.

A monitor 44 can be used for displaying images of and additional information about the golf balls as they are inspected, and also for interfacing with vision engine 42. The image of the last inspected product may be displayed on monitor 44 so that operators may see the results of the inspection analysis, particularly if a defective golf ball has been detected. Highlights and color error markers can be set to emphasize important features or problems in the image displayed on monitor 44. A freeze frame feature may be provided to freeze a defect on the screen of monitor 44 for close scrutiny while inspection continues. Such a feature also permits the image to be stored and displayed so that the operator may view the areas found defective by analyzer 32 while allowing the inspection process to continue. The frozen image remains displayed for an amount of time specified by the operator or until manually reset.

Additionally, a variety of menus and other special programs relevant for the inspection process may be displayed by monitor 44. For example, pop-up menus, overlays, on-line help messages, and helpful highlights can be used during the inspection process and may overlay the area that is being inspected and pinpoint defects as they occur. Accordingly, monitor 44 may be used as an on-screen trouble shooting guide to detect and correct hardware or software problems which might affect the system.

Preferably, an interface mechanism 46, such as a keypad, a separate set of keys, a mouse, or a touch sensitive area on monitor 44 is provided. Interface mechanism 46 preferably is provided with a variety of selectors for a variety of different functions. For example, command selectors (such as for changing on-screen images and manner of display, e.g., with or without a menu overlay or highlight and error markers), input selectors (such as numeric keys which may be used, for example, to navigate through the menu or to set parameters such as brightness), function selectors (such as alphabetical keys, e.g., A–F, used for selecting pop-up menus or for parameter adjustments), and other desired separately identifiable selectors may be provided.

Thus, analyzer 32 can monitor the manufacturing process (including output quality), automatically track the production process, and generate statistics such as the total acceptable and defective products. Additionally, analyzer 32 may be used to communicate production and status reports directly to an operator or to a host computer in a known manner. For example, analyzer 32 can report, such as to an operator or a programmable controller, inefficiencies such as cyclic defects, consecutive defects, percentage of defects, percentage yield, and/or forecasted yield. Because analyzer 32 can record the exact nature of a defect and also can provide a fast accurate breakdown of the types and quantities of each defect, analyzer 32 can be used to diagnose the precise problem in processing apparatus 14 causing the detected defect.

Analyzer 32 also may be equipped to emit a signal or an alarm to notify the operator to review and analyze the defect image and determine what, if any, correction to processing apparatus 14 is necessary. Additionally, computer-generated error flags can be used to highlight defective areas of the product being inspected. This provides an immediate indication of the detected defect and the reason the golf ball was determined to be defective.

In addition to providing on-screen information and analyses, analyzer 32 may be used to generate concise, production history reports of the inspection statistics, e.g., number of defects, percentages, and production trends. Production reports generated by analyzer 32 may include production totals or percents displaying the number of defective and acceptable products inspected, track production trends, throughput, various defect statistics, or defect results on a routine by routine basis. Such reports may be used to determine the general nature of various defects encountered in production and thereby to permit the operator/manufacturer to rectify any problems with or generally improve the system so as to result in improved production quality. Further, analyzer 32 may generate, or information provided by analyzer 32 may be used to generate, production charts graphically depicting the results, gathered over a period of time, of statistics pertaining to acceptable and defective products, relevant to overall production and/or individual production processes.

In addition to analyzing at least one characteristic of the golf ball being viewed, automated analyzer 32 also generates an analysis signal to affect the processing of the golf ball being inspected. Preferably, such signal is sent to an inspection responsive device 20, as shown in FIG. 1, which performs a specified task based on the results of the analysis performed by analyzer 32. The specific inspection responsive device 20 to be used depends on the process being performed on the golf ball as well as the next process to be performed. For instance, inspection responsive device 20 may include reject and/or sorting mechanisms, programmable controllers for feedback to the production machinery, and production alarms or indicators which indicate a fundamental problem in the production equipment.

In one embodiment, a time delay for a controlled duration depending on production speed and station set-up, e.g., the distance between detecting apparatus 36 and inspection responsive device 20, is implemented both between detection (by imaging system 30) and analysis (by analyzer 32) and between analysis (by analyzer 32) and analysis signal communication (to inspection responsive device 20) to insure that the appropriate golf ball is acted upon. In a preferred embodiment, each golf ball 66 is inventoried (i.e., tracked) as it passes through process station 10 so that inspection responsive device 20 may be positioned at any location and activated at any time after inspection. Thus, with such tracking, no time delay is necessary because a signal indicating the particular ball present at a station is provided upon arrival of that particular ball, permitting a process appropriate to that particular ball to be performed.

A position detector 48 may be used to determine the position of the golf ball between automated inspection system 12 and inspection responsive device 20 so that the appropriate inspected golf ball is acted upon by inspection responsive device 20. Any position detector known in the art, such as a detector determining absolute position, may be used. Means for determining and monitoring the velocity of the assembly line may also be provided to ensure further accuracy in determining the position of the golf ball to be acted upon. For example, a tach encoder may be useful in determining production rate for comparison with the analysis rate with which analyzer 32 may operate effectively. Alternatively, vision engine 42 may be appropriately programmed to send a signal to inspection responsive device 20 at the appropriate time as determined by the production line speed and the spacing from the individual detecting apparatuses 36. In a preferred embodiment, a computer processor is utilized to track each ball as it passes through process station 10. The computer processor sends a signal to a particular processing station to indicate the particular ball which has arrived at the processing station 10 so that the process appropriate to that particular ball may be performed. The computer processor may be provided in any form desired, as known to those of ordinary skill in the art. For example, a programmable logic controller ("PLC") could communicate with analyzer 32 to track each ball. Each ball also or alternatively may be tracked by a computer to which signals from analyzer 32 are transmitted.

Figure 3:
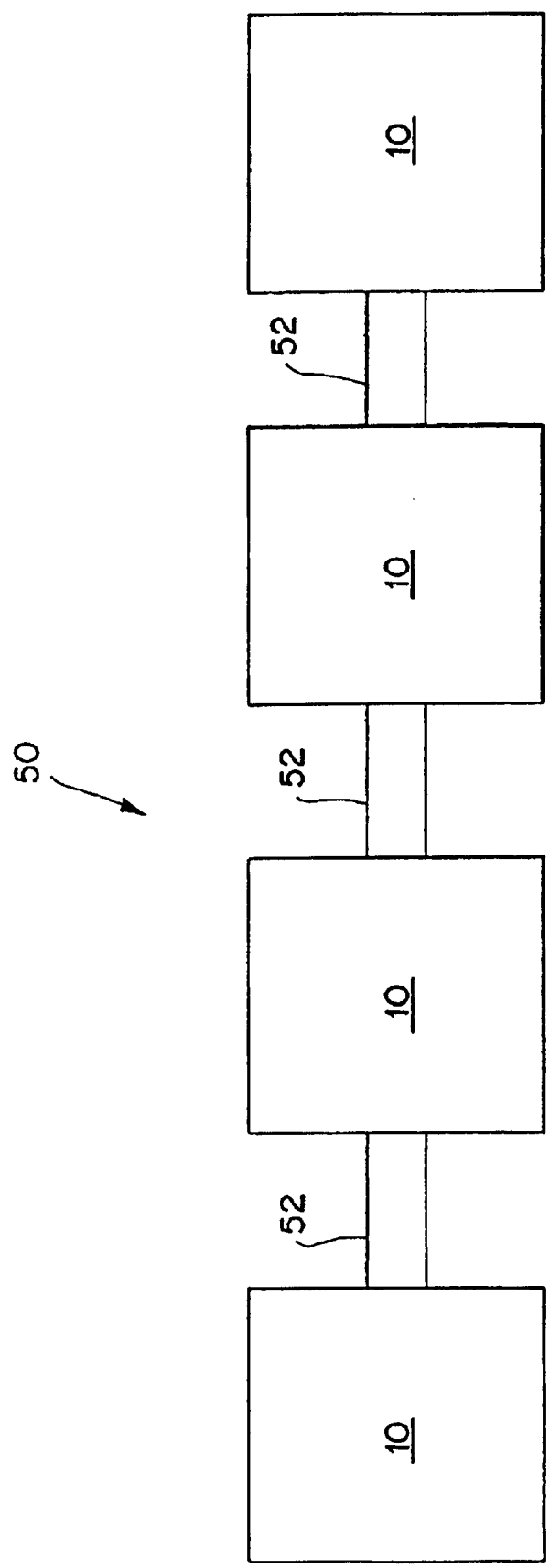
FIG. 3 is a schematic diagram of a golf ball manufacturing plant formed in accordance with the principles of the present invention.

Preferably, as illustrated schematically in FIG. 3, in accordance with the principles of the present invention, golf ball manufacturing plant 50 has multiple processing stations 10, each station performing a different operation in the golf ball manufacturing process. The golf balls are transferred by an automated transfer mechanism 52, such as a conveyor belt, between processing stations 10. Thus, progression of the golf ball from station to station is independent of human handling and thus independent of human error and delay. The provision of an automated inspection system 12 as described above in the processing stations (preferably, but not necessarily, in each station) permits defects to be detected despite the lack of human operator interaction with the processes being performed. Human intervention, at least for the purposes of quality control, thus is necessary only upon detection of a defective golf ball in the otherwise fully automated manufacturing plant.

Thus, in accordance with the principles of the present invention, every golf ball may be automatically and immediately inspected after completion of each, or at least a selected, processing step. The speed of inspection is rapid enough so that normal production rates need not be modified to permit continuous, constant inspection by automated inspection apparatus 12, so that a rapid, accurate, objective quality inspection of the golf balls processed at station 10 may be achieved. Moreover, because the inspection is automated, every golf ball processed by processing apparatus 14 is inspected.

As noted above, if desired, automated inspection system 12 may be installed at each processing station where a substance is applied to the surface of a golf ball. In any such processing station, although a similar automated inspection system 12 as described above may be used, variations in system settings and set-up typically must be made to account for differences in the process being inspected. The following exemplary applications of an automated inspection system to a golf ball processing station in accordance with the principles of the present invention illustrate particular modifications to above-described automated inspection system 12 for use with a particular processing station. It will be appreciated that the present invention is not limited to only the particular modifications described herein.

Figure 4:
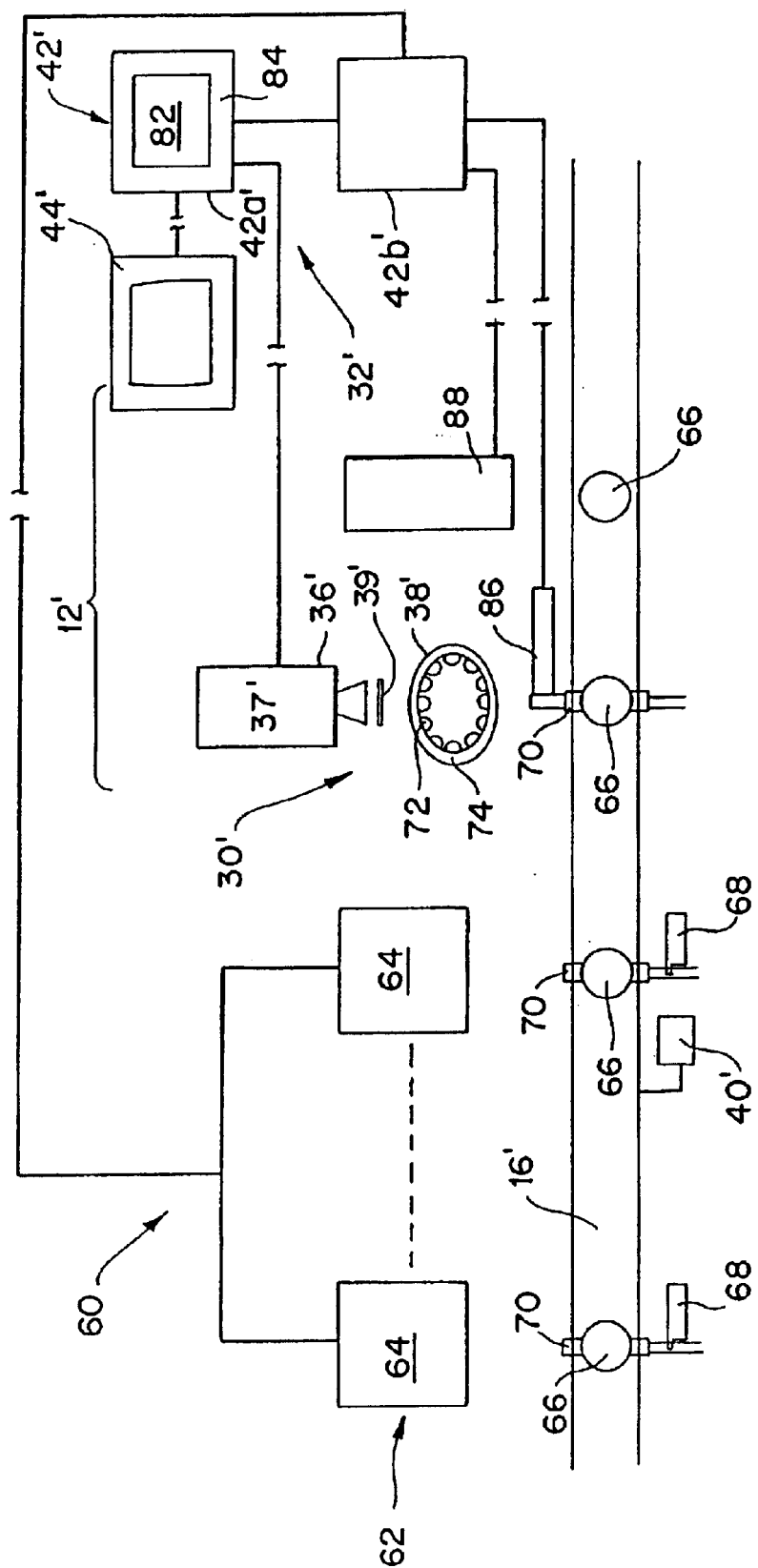
FIG. 4 is a schematic illustration of a golf ball production printing station with an automated inspection system in accordance with the principles of the present invention.

Referring to FIG. 4, a first embodiment of the automated inspection system 12' of the present invention is used in an indicia application station 60, which can be a production print station, a custom logo print station or other station where a substance is applied to create a marking on the surface of the ball. The indicia application station 60 includes an application apparatus 62 and automated transfer mechanism 16', e.g., a screw conveyor. Indicia application apparatus 62 preferably includes a printing mechanism 64 such as a pad printing mechanism for providing a production print on golf ball 66. Preferably, production prints are spaced apart over the surface of golf ball 66. Thus, an indexing mechanism 68, such as a dog, preferably is associated with each indicia application mechanism 64 and is configured and positioned to engage golf ball support 70 (such as via a pin on a wheel coupled to golf ball support 70) to rotate golf ball support 70 and hence golf ball 66 to vary the surface presented to each indicia application mechanism 64. Typically, indexing mechanism 64 is passive, indexing occurring by virtue of golf support 70 moving past a stationary indexing mechanism 64.

Once the printing process has been completed, golf ball 66 bearing indicia is preferably automatically transferred, such as by the same automated transfer mechanism 16' used to transfer golf balls between application mechanisms 64, to inspection system 12' formed in accordance with the principles of the present invention. Inspection system 12' includes an imaging system 30' formed in accordance with the principles of the invention substantially as described above in connection with imaging system 30. Imaging system 30' includes detecting apparatus 36' and environment modification device 38' configured to detect indicia on a golf ball and generate an image thereof for analysis by an analyzer 32', as will now be described. Preferably, a product sensor 40' is also provided to signal imaging system 30' of the approach of a golf ball 66 to be viewed and inspected. In a preferred embodiment, automated transfer mechanism 16' is in the form of a screw conveyor driven by a cam, and product sensor 40' monitors the position of the cam to determine progression (and hence location) of golf ball 66 as a result of the turning of the screw conveyor.

Detecting apparatus 36' preferably includes optics or at least one camera capable of acquiring or generating images with sufficient speed to not interfere with the highest achievable speed of application apparatus 62 as well as indexing mechanism 68. Preferably, the field of view is digitized to about 640×480 or higher pixel video image or any other image permitting sufficient resolution for effective analysis of the indicia as described below. Most preferably, a still image of the golf ball is generated. For example, a standard digitized shuttered camera producing a clean still image, such as a Sony Camera Kit 320-0013 or equivalent, may be used to produce the desired image. Camera 37' may be mounted to the frame of production print apparatus 62 to minimize camera vibration and blurring of camera images. The location of camera 37' is selected and the camera support structure is designed to avoid interference with the operation of application apparatus 62, and to avoid blocking access to quality check and maintenance access points.

As described above, in accordance with the principles of the present invention, an environmental modification device 38' preferably is provided to facilitate acquisition of an electronic image of the ball being inspected. For example, the environmental modification device may create a diffuse, uniform illumination of the production print which is readily detected by detecting apparatus 36' and analyzed by analyzer 32'. Such lighting preferably is provided by a specially configured lighting which floods out or otherwise causes uniform light reflection on the outer surface, including the dimples, of golf ball 66, thereby eliminating glares, shading, and image distortion that can be caused by other types of light sources used in prior machine vision systems. As described above, polarizing filter 39' may be utilized to further reduce glare. Alternatively, or in addition to the use of polarizers, the golf ball surface may be dried prior to inspection in order to further reduce glare. Because drying of the ball surface is not critical to the invention, however, any steps taken to assist drying the ball, if at all, can take place anytime before or after inspection.

As shown in FIG. 4, a preferred embodiment of the environmental modification device 38' is in the form of a plurality of light-emitting diodes (LEDs) 72 mounted over the golf ball to be inspected to provide a constant and even light source. Preferably, at least eighteen LEDs 72 are used to illuminate the golf ball. Most preferably, about thirty LEDs 72 are mounted on a support ring 74 such that camera 37', positioned above environmental modification device 38', may view the golf ball therethrough. LEDs 72 preferably are substantially evenly spaced apart and angled or directed toward golf ball 66 such that light is evenly and diffusely reflected off of golf ball 66 and substantially all shading due to surface contours is eliminated. As described above, a plurality of different color LEDs 72 may be utilized to achieve the desired illumination of golf ball 66. Preferably, the LED colors are red, green, and blue and are arranged sequentially on a support ring 74 so that, when illuminated, they combine to provide a white light of greater intensity than ordinary white light LEDs. One advantage of using different color LEDs that combine to provide a greater intensity of light is that shading or shadows caused by surface contours is eliminated. Yet another advantage of using different color LEDs, as would be appreciated by one skilled in the art, is the ability to control color of the light used during inspection. It will be appreciated that the LEDs, whether all of the same color (such as white) or of different colors, may be arranged in any desired orientation, preferably selected to provide the desired intensity and diffuse lighting effect.

Figure 5:
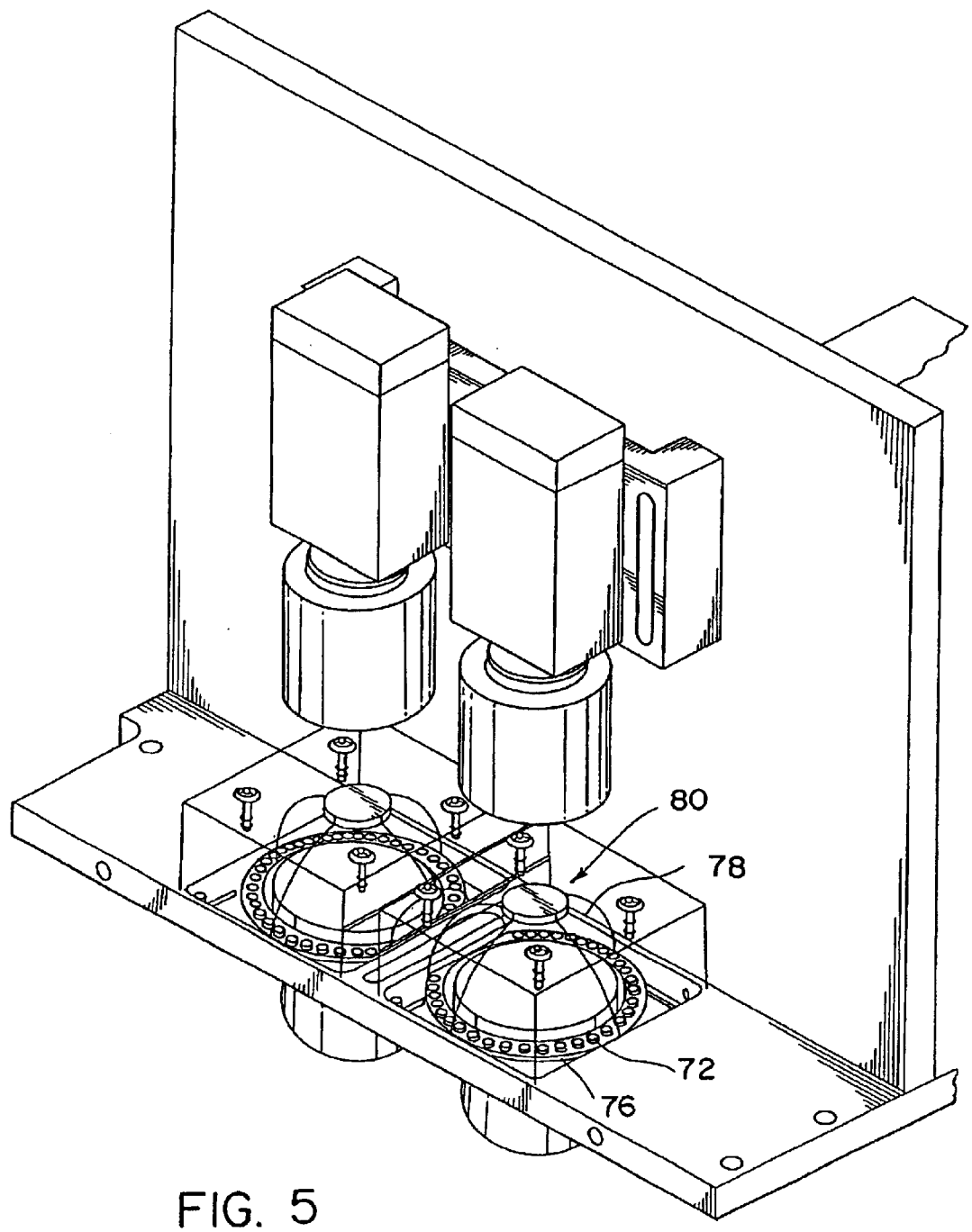
FIG. 5 is a perspective view of an environmental modification device which may be used in the automated inspection system of FIG. 4.

In an alternative embodiment, as shown in FIG. 5, a ring of upwardly directed LEDs 72 are mounted with equal spacing around the inner base 76 of a dome reflector 78 to face directly into top 80 of dome 78. The inner surface of dome 78 is provided with a coating to reflect and diffuse light emitted by the LEDs down to golf ball 66 at many different angles based on angles of reflection from all of LEDs 72. Thus, light strikes at appropriate angles of incidence such that the surface of golf ball 66 is evenly illuminated.

As described above with reference to the generic inspection system 12 shown in FIG. 2, camera 37' of production print inspection system 12' looks at a first surface area of golf ball 66 and transfers a signal of the image thereof to analyzer 32' to determine various characteristics of the indicia such as location, shape, and clarity. Analyzer 32' includes vision engine 42a' for analyzing the indicia on golf ball 66. Vision engine 42a' preferably includes a machine vision processing board 82 installed in a processor or computer 84 to acquire, analyze, store, and buffer the golf ball images transferred thereto by detecting apparatus 36' and to provide signal processing for the analysis of the images. Machine vision processing board 82 preferably is any processing board with sufficient processing capability to run the desired analysis algorithm software, such as an 8110XE vision system manufactured by Cognex Corporation of Natick, Mass. Computer 84, is selected to enhance speed and accuracy, and preferably is a Pentium™ MMX processor, manufactured by Intel Corporation of Santa Clara, Calif., running a windows-type operating system.

In a preferred embodiment, vision engine 42a' combines multiple image processing techniques, such as one or more analysis algorithms to analyze a variety of aspects of the golf ball image transmitted thereto to determine whether the image conforms with the characteristics of a reference image template. Additionally or alternatively, such algorithms determine whether extraneous marks are present. Thus, print defects including, without limitation, missing characters, ink smudges or smears, shadowing, missing sections of print, partial or complete character thickness deviation, excess or extraneous ink marks, print alignment with other print, may be detected by the system of the present invention such that proper action may be taken to eliminate the cause of such defects.

The algorithms performed by vision engine 42a' may include one or more of the following algorithms described in further detail below: an image correlation or alignment algorithm to align the inspected image for further analysis, a discrete element detection algorithm to determine if the correct number of patterns are present, an element boundary detection and characterization algorithm to determine the precise shape of the patterns, a thickness measurement algorithm to determine the thickness of individual marks, and a pattern detection and characterization algorithm to compare a pattern print on a golf ball with a reference pattern. Several or all such algorithms, as well as or alternatively other algorithms may be used. However, a combination of algorithms generally results in a more accurate inspection than achievable by separate use of any one algorithm.

The above-mentioned alignment algorithm aligns the indicia image to be inspected with a constant fixture point and angle. Once such alignment has been performed, further analysis of the characteristics of the indicia image being inspected may be performed against the characteristics of a reference image. The alignment algorithm may be Search™ or PatMax™ Align tools from Cognex Corporation of Natick, Mass., or a similar algorithm not previously applied to golf ball inspection systems.

The above-mentioned discrete element detection algorithm preferably utilizes industry standard blob analysis tools which count the number of discrete elements in the viewing area. In a vision system, a discrete element typically is identified as a continuous area of dark pixels exceeding a specified gray scale value without a break. The blob analysis thus may be used to detect excess marks, such as doctor blade marks, smudges, or drops, other than the desired elements of the indicia.

The above-mentioned boundary detection and characterization algorithm is used to determine the precise shape of the image being inspected and compare such shape with that of a reference image for conformity therewith. Preferably, an algorithm which may detect defects as small as 0.002 inches while keeping the number of false detections below 1% is used, such as the Boundary Tracker™ algorithm developed by Cognex Corporation. The Boundary Tracker™ algorithm, which previously has not been used for golf ball indicia quality inspection, creates a boundary outline, preferably on a sub-pixel level, around each discrete element of indicia being inspected. Preferably, both outer and inner boundaries (e.g., as applied to the letter "e", both the entire outer perimeter surrounding the letter as well as the enclosed inner perimeter of the top half of the letter). The boundary is broken down, such as into small line segments and arcs, to create a geometric representation which may be modified based on a best fit algorithm to match the current golf ball being inspected to a reference image (e.g., an image generated from scanning and storing a number of indicia considered to meet preselected standards or quality control criteria). The sensitivity preferably may be set to changes in the segment and arc specifications and allowed to morph as necessary, such as with changes in print thickness over time or from image to image. The algorithm searches for breaks or significant changes in contour along the boundary, missing ink inside each boundary, and excess ink, marks, smudges, or doctor blade marks outside each boundary. Additionally, the boundary detection algorithm may calculate the relative positions of pairs of indicia, such as a logo and a number, to assure correct positioning.

The above-mentioned thickness measurement algorithm is used to measure the width of an element of indicia at various points along the indicia and between opposite boundaries. Thus, the thickness measurement algorithm looks at the perimeter of each discrete element of an indicium. Typically, such algorithm is used in conjunction with the boundary detection algorithm which has generated data pertaining to the image boundary. The measured width is then analyzed to determine whether or not the indicia thickness falls within acceptable limits.

The above-mentioned pattern detection and characterization algorithm is used to compare the pattern detected in an inspection image (i.e., an inspection pattern) with a pre-defined reference pattern. The pattern detection algorithm, such as the Pat Inspect™ algorithm developed by Cognex Corporation, which has not previously been used for golf ball indicia quality inspection, compares the pattern, pixel gray scales, and/or pattern size with the reference image.

Preferably, the algorithm compares geometric shapes rather than performing an individual pixel-by-pixel analysis. While the inspection pattern need not perfectly match the reference pattern, a rejection signal will result if the pattern under inspection differs from the reference pattern by a significant amount. The degree of acceptable difference between an inspection pattern and a reference pattern may be predetermined by the user or allowed to morph as necessary, such as with changes in printing from time to time or from image to image. Such an algorithm permits more flexibility and achieves higher vision quality to match higher manufacturing and cosmetic standards and/or capabilities. This algorithm also allows more variance in golf ball orientation during inspection without affecting inspection results. Moreover, smaller images are easier to analyze on the basis of pattern rather than by analyzing all borders of the image.

The results of the algorithms preferably are transferred to a control system 42b' preferably including a processor capable of receiving signals from analyzer 32' and using such signals to control devices associated with indicia and inspecting. Preferably, a programmable logic controller ("PLC") such as an SLC505 processor and associated I/O cards sold by Allen-Bradley, a Rockwell Automation Company of Milwaukee, Wis., is used. PLC 42b' communicates with and preferably further controls independent or integrated operation of application apparatus 62' and inspection system 12' based on the analysis performed by vision engine 42a'.

Additionally, PLC 42b' may be used to control indexing of the golf ball being inspected such that all indicia thereon are viewed and analyzed. In accordance with the principles of the present invention, an indexer 86 is provided to index the golf ball being inspected until all indicia have been inspected and analyzed. Indexer 86 preferably indexes golf balls 66 by contacting the same mechanical element contacted by above-described indexing mechanism 68. However, indexer 86 preferably, in contrast, is an active indexer actuated by PLC 42b' to actively index golf ball 66 after each indicium has been inspected. In a preferred embodiment, indexer 86 is a metal arm with a suspended dog actuated by an air cylinder to rotate the golf ball 66 being inspected. Preferably, spring-tensioned clamps, on a plate clamped in place to allow only one axis of movement while the balls are moved out of the printing operation, are provided. The golf balls are rotated by indexer 86 consistently to place the next indicium in the vision system viewing area (below imaging system 30') preferably within ±0.01 inches of the same location to assure that imaging system 30' can accurately identify and center each indicium on the golf ball.

PLC 42b' also may be used to classify the golf ball being inspected as perfect, rejectable with a minor defect, or rejectable with a major defect by controlling the transfer of golf ball 66 from imaging system 30'. In one embodiment, a pick and place mechanism 88 is provided to transfer golf balls with indicia conforming with quality control criteria to the next processing station and/or to transfer golf balls with indicia not meeting quality control criteria to a reject bin. Thus, pick and place mechanism 88 may be used to transfer golf balls regardless of the results of the production print inspection, or may select only acceptable or defective golf balls, leaving the others to continue along automated transfer mechanism 16'. Pick and place mechanism 88 may be in the form of an automated transfer mechanism such as a robotic arm with vacuum plungers, a clamping device that engages with the ball, or other devices known in the art for transferring golf balls. In another embodiment, rejected and accepted balls may be separated through use of a diverter that communicates with the PLC 42. Such diverters may include, without limitation, a sliding gate operated by pneumatic or solenoid devices that direct rejected balls to a reject bin and transfer accepted balls to the next processing station.

Analyzer 32' of vision engine 42a' preferably generates an image of any defects via monitor 44' for an operator to examine so that measures may be taken to correct the cause of the defect or improve the production process. In a preferred embodiment, the operator is prompted, regardless, to check the balls to confirm that the indicia conform to quality control criteria and that inspection system 12' is functioning properly. An acknowledge button may be provided to interface with analyzer 32' to continue with the production inspection mode.

Thus, an inspection system formed in accordance with the principles of the present invention may be applied to an indicia application station 60 in a golf ball manufacturing process, such as process 50 of FIG. 3, to achieve a high enough level of accuracy to provide on-line indicia quality inspection. In particular, inspection system 12' includes specific lighting, optics and ball indexing methods which provide a clear undistorted image of each indicia applied to the surface a golf ball to the image processing system. The combination of signal processing, image analysis, and image grading algorithms performed on the indicia images permit accurate inspection which reduces, if not eliminates, the need for human intervention during processing.

Figure 6:
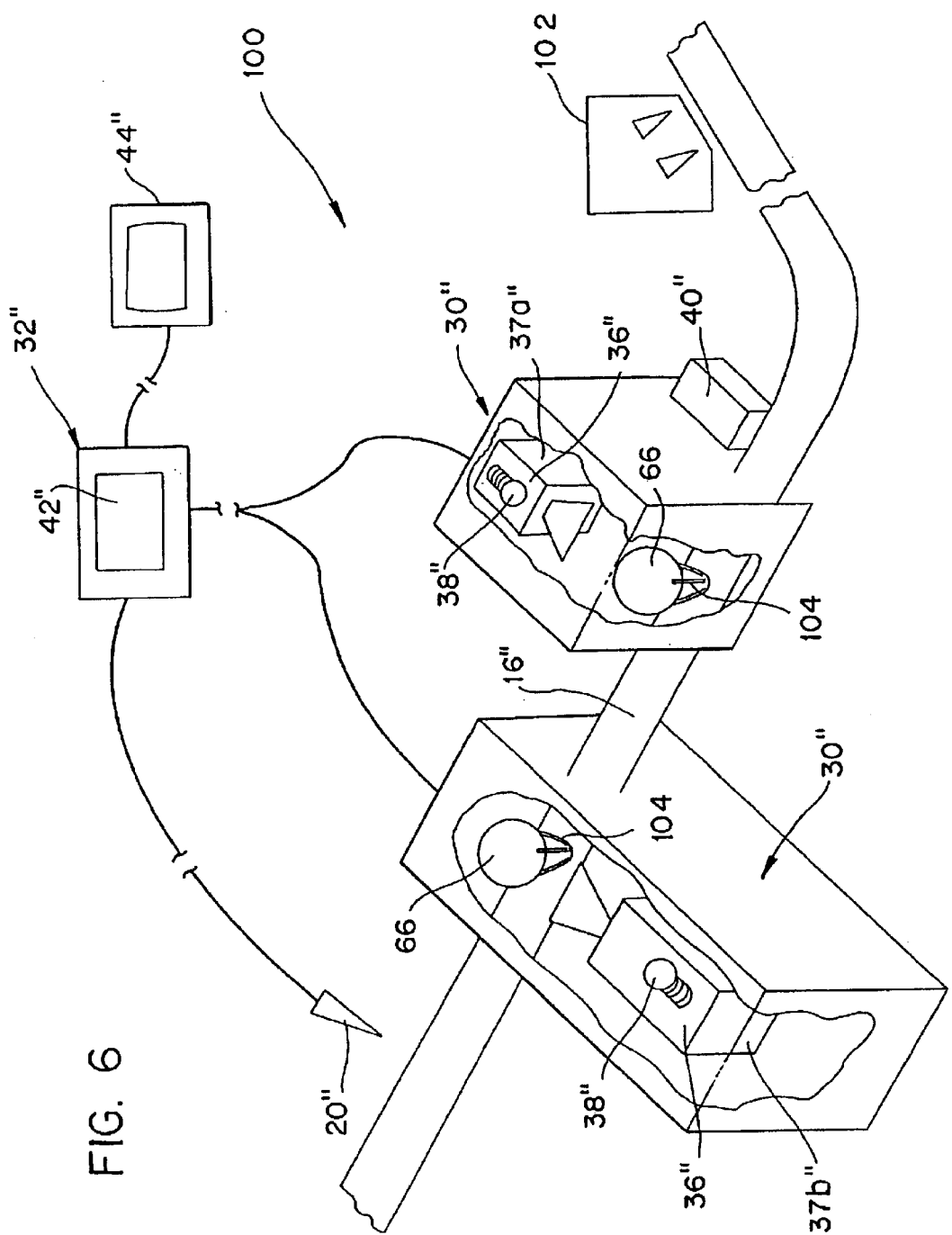
FIG. 6 is a schematic illustration of a golf ball spray painting station with an automated inspection system in accordance with the principles of the present invention.

Referring now to FIG. 6, another processing station 10 in which automated inspection system 12 may be utilized is a paint spray station 100 at which a coating such as a clear coat, primer, paint or other substance is sprayed onto the golf balls in a paint spray booth 102. It will be appreciated that although reference hereinafter is made to spray painting of a clear coat, the principles of the present invention are not so limited and may be applied to application of other materials such as paints as well.

In order to automate the inspection of the spray painted golf balls, the golf balls exiting paint spray booth 100 are passed directly to automated inspection system 12", which is provided as an integral part of the processing station. Preferably, golf balls 66 rest on a three prong seat 104, to reduce handling as well as to permit inspection of almost every side by imaging system 30".

Detecting apparatus 36" views the exterior surface of golf ball 66. A product sensor 40" may be provided in adjacent imaging system 30, such as on top of or to the side of detecting apparatus 36" or an enclosure in which detecting apparatus 36" is housed, to assure that images of golf balls 66, and not empty golf ball seats 104, are transmitted by imaging system 30" to analyzer 32". Preferably, detecting apparatus 36" of imaging system 30" includes at least two cameras 37" (or other form of detecting apparatus) positioned on opposite sides of the path 34" along which the ball travels to view a substantial portion of the ball being inspected. Thus, a first camera 37a" may view a first portion of the ball surface and a second camera 37b" views a second portion of the ball surface, such that substantially the entire ball surface is viewed by detecting apparatus 36". Because golf ball 66 typically rests on a stand 104, stand 104 may block viewing of certain portions of golf ball 66, which may give a false reading of the presence of clear coat at the blocked area of golf ball 66. Accordingly, cameras 37" preferably are positioned such that stand 104 does not interfere with viewing. For instance, each camera 37" may be angled downward, such as 20°–30° from horizontal, towards golf ball 66. With such configuration, opposing surfaces of golf ball 66, with some overlap, are viewed.

Typically, in order to facilitate inspection, the clear coat is provided with an agent or element detectable by varying at least one environmental condition, but which is not normally detectable in ambient conditions. The presence of such element is indicative of the presence of the clear coat on golf ball 66, such that evaluation of such element may be used to determine the coverage characteristics (e.g., presence, adequacy, or sufficiency) of the clear coat. Because such element preferably is not detectable under ambient conditions, environment modification device 38" of automated inspection system 12" is selected to permit detection of the element added to the clear coat.

The element provided in the clear coat may be an agent, such as a fluorescent agent, which illuminates upon exposure to certain wavelengths of light. Environment modification device 38" thus provides lighting which emits a wavelength other than ambient selected to illuminate such agent. For example, an ultraviolet ("UV") agent, such as Eastobrite OB-1 optical brightener (manufactured by Eastman Chemical Company of Kings Point, Tenn.) illuminated by light of wavelengths of 300–400 nm, especially 365 nm, may be added to the clear coat. Inspection of the ball under UV light, e.g., black light, permits the UV agent in the clear coat to be detected so that the clear coat coverage may be analyzed. It will be appreciated that any other agent that is detectable under changed environmental conditions (not limited to lighting) may be used instead. Coverage, such as location and sufficiency of the clear coat as well as differences in thicknesses of the clear coat and other characteristics, may be determined by analyzing the distribution and intensity of the agent detected in the clear coat.

Because the clear coat typically is applied over a production print or other ink application, it is preferable that image detectors or cameras 37 detect the presence of the agent in the clear coat in a manner that would not be affected by light and dark areas below the clear coat. In accordance with the principles of the present invention, presence of the agent in the clear coat is detected using a similar scale for detecting the presence of indicia so that detection of indicia (typically a dark area under ambient light) will not falsely trigger insufficiency or absence of clear coat coverage (typically a dark area under the special, e.g., UV, lighting). For example, a filter which detects fluorescence of the agent as "dark" and absence or low quantity of the agent as "light" may be used for the camera 37.

The environmental modification device 38" is preferably comprised of a plurality of UV lights 106 for each camera 37". Preferably, the environmental modification device is comprised of at least one UV light 106 positioned above the camera 37" and another UV light (not shown) positioned below the camera 37" to substantially eliminate any shading or shadowing due to the ball surface contours. It will be appreciated that because environmental modification device 38" includes the lighting devices 106 which must be near each camera 37", if cameras 37" were positioned directly opposite each other and facing each other, then lighting of one camera 37a" would interfere with proper detection by the opposite camera 37b". Accordingly, to avoid such interference, first camera 37a" is provided on a first side of golf ball 66 at a first location along the production line and second camera 37b" preferably is provided on a second side of golf ball 66 at a second location which is preferably downstream of the first location.

Analyzer 32" of paint spray station 102 preferably includes a vision engine 42" capable of processing and analyzing data from detecting apparatus 36" as provided in imaging system 30". In a preferred embodiment, vision engine 42" provided by Advanced Technologies, Inc. or Cognex Corporation may be used, with software developed for the analysis of the specific characteristics of golf ball surfaces.

Analyzer 32" may be adapted to receive data from three (or more) paint spray stations and thus three (or more) corresponding imaging systems 30", each preferably utilizing two cameras 37" in detecting apparatus 36", for a total of six (or more) cameras 37" providing information to analyzer 32". Information pertaining to the clear coat, preferably determined by detection of the agent provided therein, generated by imaging system 30" is transmitted to analyzer 32". Vision engine 42" of analyzer 32" preferably performs a variety of preliminary analysis routines, such as shade detect, centering, and gray check routines. Preferably, the results of any or all of the analysis routines, an image of the golf ball being inspected or at least a defective golf ball, as determined by analyzer 32", is displayed via monitor 44" for examination.

The shade detect routine checks for certain percentages of a desired gray level or shade of color within a scan line. Thus, the shade detect routine is used to determine whether a ball is actually present. As described above, such determination insures that statistics on acceptable and defective golf balls will not be skewed by extraneous information.

The centering routine determines the center of the golf ball and applies this information to all inspection routines performed on that golf ball. Such a routine may include the use of x,y parameters, masks, and/or left, right, top, and bottom inspection bars to approximate the center of the golf ball being inspected.

The gray check routine detects the average gray level of a scan line along the surface being inspected. Because of the spherical exterior shape of the golf ball, the center portion of the face of the golf ball being inspected is closer to detecting apparatus 36" than a more peripheral portion of the inspected face. Thus, the gray check analysis preferably is broken down into a center scan, analyzing the central portion of the golf ball surface, and a peripheral scan analyzing the more peripheral portion of the golf ball. The gray level determined for each scan line is compared to preset minimum/maximum limits to determine the presence of the agent in the clear coat. In a preferred embodiment, the routine looks for a low gray level to determine a dark area and thus a lack of continuous clear coat coverage, signalling a defective golf ball. If desired, the analysis may instead involve comparison to a required brightness scale to determine presence, and even thickness, of the coating.

Preferably, the scan lines are arranged to extend radially outwardly from the center of the golf ball. Preferably, the scan area is broken into about 2047 computer degrees. However, different scan line patterns are within the scope of the present invention. Additionally, in order to account for the spherical contour of the golf ball, resulting in a central portion of the golf ball being closer to detecting apparatus 36" than a more peripheral portion, the inspection area is preferably separated into a central area and surrounding peripheral ring-shaped areas. For example, the central area may be from 0–147 pixels, in a generally circular shape to form the center. The peripheral ring-shaped area may be from 125–179 pixels, in a direction radially outward from and surrounding the center. It may overlap the central area for added accuracy. The increment value determines the number of scan lines to be used in a selected area. It will be appreciated that because defects must lie along the scan lines being analyzed, the scan lines should be close together to provide sufficient resolution to detect defects. However, if the scan lines are too close, gradually occurring defects are not readily detectable because the comparison between neighboring scan lines shows very small differences. Both fine and coarse symmetry analyses may be performed.

Preferably, inspection routines such as described above are performed by comparison of characteristics of the image from detecting apparatus 36" with characteristics of a reference images in the analyzer memory. Comparison may be achieved through the use of high resolution or high performance inspection algorithms as developed by one of ordinary skill in the art. Typically, the standards forming the basis for comparison are user generated specifications based on a selected number of images which have been determined to meet production requirements. Parameter values may be stored in non-volatile memory which is immune to power outages, power shut-offs, etc. Thus, the parameter data selected by the user is always available and will not require re-entering.

If a defect is detected, an appropriate signal is generated and preferably transmitted to an inspection responsive device 20". For example, analyzer 32" can send a reject signal to the production line to transfer the golf ball from the production line and into an inspection or reject bin. Thus, inspection responsive device 20" may be a reject device, such as a lever or a high speed blast of air from an air solenoid, air valve, or other air puff device, which is used to effectuate the transfer. High speed, high precision air solenoids provide an accurate rejection of defective golf balls, which are relatively lightweight, from high speed production flows, without interfering with other balls on the production line. Other reject devices, such as magnetic pick-off devices and robotic actuators, may be used instead.

Preferably, inspection responsive device 20" is set up so that the device is not falsely triggered or retriggered, such as by carefully selecting the above-described time delay between detecting a defect and rejecting the defective golf ball. Additionally, if certain rejects are detected and the system is shut down, then the production process such as paint spraying also may be shut down. For example, if the clear coat is not continuously applied, and the clear coat spray jets are inactive for a sufficient amount of time, the clear coat may harden in the spray nozzle, clogging the nozzle and interfering with further production. Thus, accuracy not only in detecting defects but also in not detecting defects which are not present, is important for quality control and production efficiency.

In accordance with the principles of the present invention, to further enhance efficiency and reduce production time, a clear coat system station 120 using a fast-drying clear coat may be used as illustrated in FIG. 7. Clear coat system station 120 is equipped with a clear coat spray booth 122, a curing oven 124, and an automated inspection system 12''' between clear coat spray booth 122 and curing oven 124. Typically, a mechanical means, such as a robotic arm 126, picks up the golf balls which have been inspected by inspection system 12''' and found to be acceptable and places the acceptable balls on a tray which enters curing oven 124. Thus, properly clear coated golf balls are automatically conveyed from the clear coat spray booth 122 to curing oven 124 within the same station 120. After approximately 30–45 minutes in curing oven 124, the golf balls exit, ready for further processing. The use of fast-drying clear coat paint, along with the combination of a clear coat spray booth 122 and a curing oven 124 in the same clear coat system station 120 streamlines the clear coat process because the clear coat paint dries in approximately one and one-half hours.

Thus, in accordance with the principles of the present invention, the application and curing of a clear coat on a golf ball may be accomplished in the same processing station without the need to transfer the golf balls from a paint spray booth to a separate curing station. Further in accordance with the principles of the present invention, an automated inspection system 12''' is used immediately after the clear coat is applied.

Additional golf ball manufacturing processes other than those described above may benefit from the use of automated inspection system 12 as described herein. For example, compression molding of such golf ball elements as the cover, creates a flash around the ball (excess material in the shape of an annular ring). Injection molding, in which material is filled through channels into a mold, leaves one or more sprues around the ball. The flash or sprues must be properly buffed down or ground away to result in the desired smooth exterior necessary for proper aerodynamic qualities. The inspection system of the present invention may be used to detect non-buffed or otherwise ineffectively finished balls having residual flash or sprue material. Typically, improperly finished exterior surfaces of elements of the golf ball, such as an improperly ground core, are identified by the detection of shiny spots through use of automated inspection system 12 programmed to detect such surface features and thereby determine the quality of the specific surface treatment affecting the contour of the golf ball. Through the use of imaging system 30 and analyzer 32 as described above, inspection of surface contours may be accomplished by analyzing a still image of a golf ball. Accordingly, there is no need to rotate the golf ball for inspection, eliminating rotating devices of prior art automated surface inspection systems.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. Moreover, it will be appreciated that although the system of the present invention is described with respect to two-piece golf balls, the inventive system may be used in the manufacture of other types of golf balls as well, such as three-piece wound and multilayer balls. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. An automated inspection system for automatically inspecting a surface treatment of a game ball, said automated inspection system comprising:

an imaging system arranged to detect the presence of a substance applied to the surface of a game ball and to generate a detection signal representative of said substance;

a light modification device provided to enhance image detection and acquisition by said image system; and an analyzer coupled to said imaging system to receive said detection signal from said imaging system and analyze said detection signal to determine conformance of the surface treatment to production standards.

2. An automated inspection system as in claim 1, wherein said light modification device comprises a plurality of color LEDs to illuminate the game ball surface.

3. An automated inspection system as in claim 2, wherein said LEDs are red, green, and blue.

4. An automated inspection system as in claim 1, wherein said lighting modification device comprises at least one polarizing filter to reduce glare.

5. An automated inspection system as in claim 1, wherein:

said imaging system comprises a detector; and said detection signal comprises a still image of the golf ball being detected.

6. A method of automatically inspecting the surface of a game ball to determine conformance of a surface treatment performed on the game ball to predetermined standards, said method comprising the steps of:

performing a surface treatment on a game ball in a processing station;

modifying the lighting conditions to permit accurate automated inspection of the treated game ball; and determining whether the surface treatment conforms to predetermined standards.

7. A method as in claim 6, wherein said step of modifying the lighting conditions comprises providing a plurality of LEDs in different colors.

8. A method as in claim 7, wherein said step of providing a plurality of LEDs in different colors comprises the step of providing red, green, and blue LEDs.

9. A method as in claim 6, wherein said step of modifying the lighting conditions comprises providing a polarizing filter to reduce glare.

10. A method as in claim 6, further comprising the step of generating an analysis signal indicative of whether the surface treatment conforms to predetermined standards.

11. A method as in claim 10, further comprising the step of utilizing said analysis signal to perform a further operation on the inspected game ball.

12. A golf ball manufacturing processor comprising:

a plurality of automated processing stations including at least a first automated processing station positioned upstream of a second automated processing station, each of said stations performing processes required for the manufacture of a golf ball;

an automated transferring mechanism arranged between at least said first and second automated processing stations to transfer golf balls between said stations without human intervention;

an automated inspection system in at least one of said processing stations upstream of an inspection response device, said automated inspection system determining whether a printed indicia on the surface of the golf ball processed in said at least one processing station conforms to production standards and may be transferred by said automated transferring mechanism to the next processing station, said automated inspection system comprising an imaging system arranged to detect the shape of indicia on a golf ball; and a tracking system storing information about each ball inspected by said automated inspection system and which said golf ball is positioned for processing such that an appropriate process is performed on a golf ball at a processing station.

13. A golf ball manufacturing processor as in claim 12, wherein said processing station includes a reject device activated by said tracking system to reject a ball not confirming to production standards.

14. An automated inspection system for automatically inspecting a surface treatment of a golf ball, said automated inspection system comprising an imaging system arranged to detect the shape of indicia on a golf ball and to compare the shape to a standard shape to determine conformance of the indicia to production standards.

15. An automated inspection system as in claim 14, wherein said imaging system detects indicia regardless of orientation of said indicia.

* * * * *